United States Patent [19]

van Andel

[11] Patent Number: Plant 7,746

[45] Date of Patent: Dec. 10, 1991

[54] CARNATION NAMED STABARVIOL

[75] Inventor: Jacob van Andel, Aalsmeer, Netherlands

[73] Assignee: Van Staaveren, B.V., Aalsmeer, Netherlands

[21] Appl. No.: 541,522

[22] Filed: Jun. 21, 1990

[51] Int. Cl.[5] ..... A01H 5/00

[52] U.S. Cl. ..... Plt./70

[58] Field of Search ..... Plt./70, 72

*Primary Examiner*—Howard J. Locker

*Attorney, Agent, or Firm*—Charles W. Rummler

[57] ABSTRACT

A new and original mini-spray carnation variety particularly distinguished by the cyclamen purple coloration of its small sized blossoms, which are produced intermittently in tight clusters during the spring, summer and fall blooming periods. The plant itself has a vigorous growth habit and a height somewhat more than 60 cm.

1 Drawing Sheet

BACKGROUND OF THE NEW PLANT

This new mini-spray carnation cultivar originated as a hybrid seedling developed by me at our nursery in Aalsmeer, Holland by crossing two varieties selected from our collection of carnations maintained for breeding purposes at Aalsmeer. This particular seedling was selected for propagation because of its unusual cyclamen purple flower coloration and the overall high quality of the plant growth. Asexual propagation of this selected plant was done by means of cuttings under my direction at Aalsmeer and propagation of this new plant in the same manner was continued from generation to generation to determine whether the novel characteristics of the selected seedling would be retained from generation to generation and its homogeneity could be assured. This proved to be successful and this new mini-spray carnation variety is now being propagated at Aalsmeer.

DESCRIPTION OF THE DRAWING

My new mini-spray carnation cultivar is illustrated by the accompanying photographic drawing, which shows blooming portions of flowering stems in full color; the color rendition being as nearly true to that herein specified as is reasonably possible to obtain by professional photographic procedures.

DESCRIPTION OF THE NEW PLANT

The following is a detailed description of my new mini-spray carnation variety based upon observation of plants grown in greenhouse as well as outdoors at Aalsmeer and blooming during the current year. The color designations stated herein are according to the R.H.S. Colour Chart published by The Royal Horticultural Society of London, England.

THE PLANT

Origin: Seedling.

Parentage:

- *Seed parent.*—Stock number 86209-2J (unpatented).
- *Pollen parent.*—D. Barbatus (unpatented).

Classification:

- *Botanic.*—Dianthus Hybrid.
- *Commercial.*—Mini-spray Carnation.

Form: Strong, erect bush.

Height: Averaging from 60 cm.

Main stem:

- *Length.*—In average, about 60 cm.
- *Growth.*—Vigorous, strong and rapid.
- *Branching character.*—Less than one shoot per node.

Foliage:

- *Number of leaves.*—Varies depending on season.
- *Leaf size.*—About 90 mm long and 8 mm wide at the fifth node.
- *Leaf shape.*—Pointed and slightly curled with entire margins.
- *Texture.*—Leathery.
- *Color.*—Both upper and under side are dark green.

THE BUD

Size: Small.

- *Diameter.*—Averaging about 8 mm.
- *Length.*—Averaging about 20 mm.

Shape: Cylindrical.

Calyx:

- *Shape.*—Cylindrical.
- *Size.*—Averaging 10 mm in width and 20 mm in length.
- *Splitting.*—The calyx does not split.
- *Aspect.*—Smooth.

Flower stem:

- *Character.*—Erect.
- *Color.*—Dark green.
- *Length.*—Averaging about 40 cm.

THE FLOWER

Blooming habit: Intermittent, during Spring, Summer and Fall blooming periods.

Size of flower: Small.

- *Diameter.*—Averaging about 30 mm.
- *Depth.*—Averaging about 1 cm.

Borne: In a tightly grouped cluster.

Shape when first opening: Flat.

- *When mature.*—High center.

Petalage:

- *Number of petals.*—Few.
- *Texture.*—Soft.
- *Appearance.*—Velvety.
- *Color.*—Both outer petals and inside petals: Body: 74A and 74B with occasional whitish longitudinal stripes, especially on the innermost petals. Base: White.

*Reverse side.*—74C.

Flower stem:

*Length.*—Averaging about 40 cm.

*Color.*—Dark green.

*Character.*—Strong and upright.

Discoloratoin after full bloom: Color becomes somewhat darker.

Persistence: The flowers hang on and dry.

Disease resistance: Resistant to *Fusarium oxysporum.*

Lasting quality: Averaging about 12 days as a cut flower and 21 days on the plant.

REPRODUCTIVE ORGANS

Stamens:

Number: Few.

*Arrangement.*—Normal. Size: Small. Color: Violet.

*Filaments.*—Length: About 25 mm. Color: White.

Pistils:

*Number.*—1.

*Styles.*—Length: About 20 mm. Color: White.

Stigmas:

*Color.*—Violet.

I claim:

1. The new and distinctive spray carnation plant, substantially as herein shown and described, particularly characterized by the cyclamen purple coloration of its small, tightly grouped flowers, and its intermittent and vigorous growth habit.

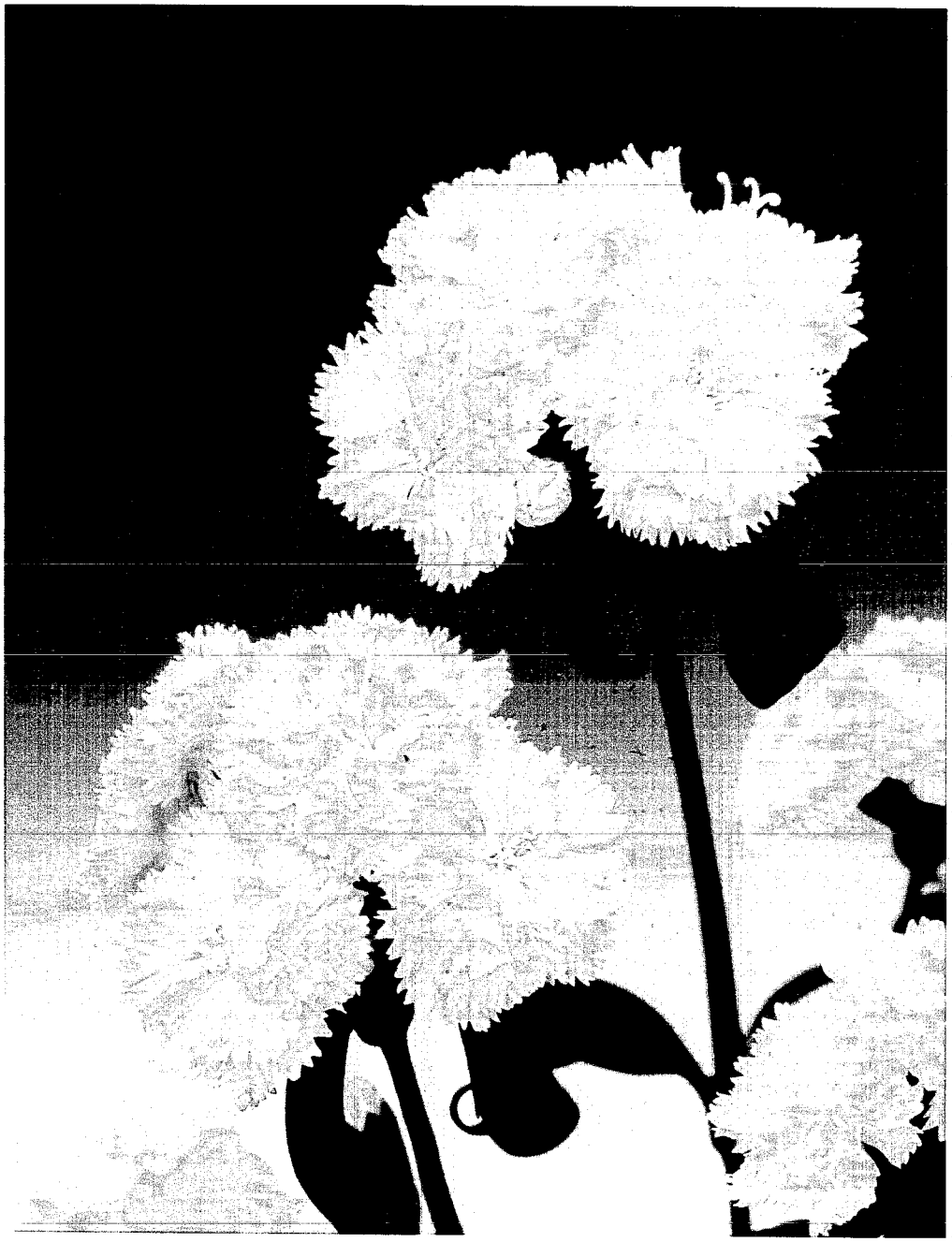

* * * * *